(12) United States Patent
Yang et al.

(10) Patent No.: US 9,470,636 B2
(45) Date of Patent: Oct. 18, 2016

(54) DEVICE AND METHOD FOR DETECTING LIQUID CRYSTAL DISPLAY PANEL

(71) Applicants: BOE TECHNOLOGY GROUP CO., LTD., Beijing (CN); CHENGDU BOE OPTOELECTRONICS TECHNOLOGY CO., LTD., Chengdu (CN)

(72) Inventors: Yinyong Yang, Beijing (CN); Hwang Kim, Beijing (CN)

(73) Assignees: BOE Technology Group Co., Ltd., Beijing (CN); Chengdu BOE Optoelectronics Technology Co., Ltd., Chengdu (CN)

( * ) Notice: Subject to any disclaimer, the term of this patent is extended or adjusted under 35 U.S.C. 154(b) by 122 days.

(21) Appl. No.: 14/122,120

(22) PCT Filed: Dec. 20, 2012

(86) PCT No.: PCT/CN2012/086972
§ 371 (c)(1),
(2) Date: Nov. 25, 2013

(87) PCT Pub. No.: WO2013/149486
PCT Pub. Date: Oct. 10, 2013

(65) Prior Publication Data
US 2014/0085636 A1   Mar. 27, 2014

(30) Foreign Application Priority Data

Apr. 6, 2012   (CN) .......................... 2012 1 0100178

(51) Int. Cl.
*G01J 4/00*     (2006.01)
*G01N 21/88*    (2006.01)
*G02F 1/133*    (2006.01)

(52) U.S. Cl.
CPC ........... *G01N 21/8806* (2013.01); *G02F 1/133* (2013.01)

(58) Field of Classification Search
CPC .......................... G02F 1/133; G01N 21/8806
See application file for complete search history.

(56) References Cited

U.S. PATENT DOCUMENTS 3,711,180 A * 1/1973 Klinger et al. ............... 359/252
3,726,584 A * 4/1973 Adams et al. .................. 349/19

(Continued)

FOREIGN PATENT DOCUMENTS

CN        1383489 A     12/2002
CN        1385888 A     12/2002

(Continued)

OTHER PUBLICATIONS

PCT International Preliminary Report on Patentability issued by the International Bureau of WIPO on Oct. 7, 2014 for International Application No. PCT/CN2012/086972, 10 pages.

(Continued)

*Primary Examiner* — Tri T Ton
(74) *Attorney, Agent, or Firm* — Banner & Witcoff, Ltd.

(57) ABSTRACT

A device and method for detecting a liquid crystal display panel (100) can perform loaded electrical signal detection on an FFS-type liquid crystal display panel (100), thereby increasing the yield of products. The device comprises a transparent bearing platform (101), a first polarizer (102), a second polarizer (103) and a backlight source (104), and also comprises a first transparent electrode layer (105) which is located above the transparent bearing platform (101); a second transparent electrode layer (106) which is located beneath the transparent bearing platform (101); a signal loading unit (109) which is electrically connected to the first transparent electrode layer (105) and the second transparent electrode layer (106) and used for loading electrical signals to the first transparent electrode layer (105) and the second transparent electrode layer (106), to enable an electric field making liquid crystal molecules of the liquid crystal panel (100) to be detected on the transparent bearing platform (101) deflect to be formed between the first transparent electrode layer (105) and the second transparent electrode layer (106).

10 Claims, 1 Drawing Sheet

(56) References Cited

U.S. PATENT DOCUMENTS

| | | | | |
|---|---|---|---|---|
| 4,514,041 | A | * | 4/1985 | Tanaka .......................... 349/96 |
| 7,379,133 | B2 | * | 5/2008 | Iijima ............... G02F 1/133555 349/102 |
| 2002/0173060 | A1 | | 11/2002 | Hiroki |
| 2003/0117164 | A1 | | 6/2003 | Fujii et al. |
| 2011/0090502 | A1 | | 4/2011 | Bai et al. |
| 2011/0273643 | A1 | * | 11/2011 | Arai .................. G02F 1/133528 349/64 |
| 2014/0085636 | A1 | | 3/2014 | Yang et al. |

FOREIGN PATENT DOCUMENTS

| | | | |
|---|---|---|---|
| CN | 1580891 | A | 2/2005 |
| CN | 101315471 | A | 12/2008 |
| CN | 101614885 | A | 12/2009 |
| CN | 101813835 | A | 8/2010 |
| CN | 102043266 | A | 5/2011 |
| CN | 102654659 | A | 9/2012 |
| JP | 2005338261 | A | 12/2005 |
| WO | 2008126988 | A1 | 10/2008 |

OTHER PUBLICATIONS

First Office Action issued by the Chinese Patent Office for Chinese Patent Application No. 201210100178.4 dated Mar. 3, 2014, 5pgs.
English translation of First Office Action issued by the Chinese Patent Office for Chinese Patent Application No. 201210100178.4 dated Mar. 3, 2014, 3pgs.
International Search Report for International Application No. PCT/CN2012/086972, 4pgs.
English translation of Chinese Patent No. 101315471, 38pgs.
English translation of Chinese Patent No. 101614885, 16pgs.
English translation of Chinese Patent No. 101813835, 20pgs.
English translation of Chinese Patent No. 102043266, 12pgs.
English translation of Chinese Patent No. 102654659, 20pgs.
English translation of Chinese Patent No. 1383489, 16pgs.
English translation of Chinese Patent No. 1385888, 116pgs.
English translation of Japanese Patent No. 2005-338261, 20pgs.

* cited by examiner

«DEVICE AND METHOD FOR DETECTING LIQUID CRYSTAL DISPLAY PANEL

CROSS REFERENCE TO RELATED APPLICATIONS

This application is based on International Application No. PCT/CN2012/086972 filed on Dec. 20, 2012, which claims priority to Chinese National Application No. 201210100178.4 filed on Apr. 6, 2012, the contents of which are incorporated herein by reference.

TECHNICAL FIELD

Embodiments of the present invention relate to a device and method for detecting a liquid crystal display panel.

BACKGROUND

A liquid crystal display panel mainly includes a color filter substrate and a Thin Film Transistor (TFT) array substrate that are cell-assembled together, and a liquid crystal layer is sandwiched between the color filter substrate and the TFT array substrate. In the production process of the liquid crystal display panel, in order to spot quality problems in the liquid crystal display panel as soon as possible, it is necessary that a Q-panel (¼ panel) substrate should be detected during manufacture. As for the Q-panel substrate, it is detected chiefly by using an optical detection method. Namely, polarizers are located over and under the Q-panel substrate, respectively, and a voltage signal is loaded to a pixel electrode of the substrate, so that an electric field is produced between a TFT substrate in the Q-panel substrate and a color filter substrate, and in turn, liquid crystal molecules are deflected under the action of the electric field. When the light emitted from a backlight source is incident into the liquid crystal display panel, a detection personnel can watch the light passing through the Q-panel substrate, and then perform detection on the substrate.

However, due to drawbacks in design, a Fringe Field Switching (FFS) mode Q-panel (¼ panel) substrate does not reserved an electrode terminal side at present. Thus, detection cannot be performed at the stage of cell-forming by application of an electric signal to the electrode terminal side like a Twisted Nematic (TN) mode Q-panel substrate with a reserved electrode terminal side, and only an Electrical Test (ET) detection can be performed after a mother plate is cut for the second time. Such a detecting method has big limitations, increases the risk during the production of the FFS mode Q-panel substrate, and has the potential to cause big losses.

SUMMARY

The embodiments of the invention provide a device and a method for detecting a liquid crystal display panel, capable of performing a detection with an electric signal loaded on the liquid crystal display panel, such as an FFS mode liquid crystal display panel, so that the yield is enhanced.

In an aspect of the invention, there is provided a device for detecting a liquid crystal display panel, comprising: a transparent bearing platform for bearing the liquid crystal display panel to be detected; a first polarizer positioned over the transparent bearing platform; a second polarizer positioned under the transparent bearing platform; a backlight source positioned below the second polarizer, wherein light emitted from the backlight source arrives at the first polarizer after passing through the second polarizer and the transparent bearing platform; a first transparent electrode layer provided over the transparent bearing platform; a second transparent electrode layer provided under the transparent bearing platform; a signal loading unit, electrically connected to the first transparent electrode layer and the second transparent electrode layer, for loading an electric signal to the first transparent electrode layer and the second transparent electrode layer, so that an electric field for allowing liquid crystal molecules of the liquid crystal display panel to be detected on the transparent bearing platform to deflect is formed between the first transparent electrode layer and the second transparent electrode layer.

In another aspect of the invention, there is provided a method for detecting a liquid crystal display panel, a first polarizer is provided over a transparent bearing platform; a second polarizer is provided under the transparent bearing platform; a backlight source is provided below the second polarizer; a first transparent electrode layer is provided over the transparent bearing platform; a second transparent electrode layer is provided under the transparent bearing platform; and a signal loading unit is provided to connect to the transparent electrode layer and the second transparent electrode layer; the detection method comprising: loading the liquid crystal display panel to be detected onto the transparent bearing platform; loading an electric signal to the first transparent electrode layer and the second transparent electrode layer by the signal loading unit, so that an electric field allowing liquid crystal molecules to deflect is formed between the first transparent electrode layer and the second transparent electrode layer; allowing light from the backlight source to transmit through the second polarizer and the transparent bearing platform to arrive at the first polarizer; performing detection on the liquid crystal display panel with the light arriving at the first polarizer.

With respect to the device and method for detecting a liquid crystal display panel provided by the embodiments of the invention, for example, when an FFS mode liquid crystal display panel is detected, above and below liquid crystals there is formed a planar electric field to make liquid crystal molecules in the liquid crystal to deflect, allowing the light emitted from a backlight source to pass through liquid crystals. Thus, the detection on the liquid crystal display panel is realized, and yield is enhanced.

BRIEF DESCRIPTION OF THE DRAWINGS

In order to illustrate the technical solution of the embodiments of the invention more clearly, the drawings of the embodiments will be briefly described below; it is obvious that the drawings as described below are only related to some embodiments of the invention, but are not limitative of the invention.

DETAILED DESCRIPTION

In order to make the technical objects, technical details and advantages of embodiments of the invention more clearly, hereinafter, technical solutions of the embodiments of the invention will be described in a way that is clear and complete in combination with accompanied drawings of the embodiments of the invention. It is obvious that the described embodiments of the invention are just a part but not all of the embodiments of the invention. Based on the described embodiments of the invention, those ordinarily skilled in the art can obtain other embodiment(s), without any inventive work, which come(s) into the scope sought for protection by the invention.

Unless otherwise defined, the technical terminology or scientific terminology used herein should have the same meaning as commonly understood by one of ordinary skill in the art to which this invention belongs. "First", "second" and the like used in specification and claims of the patent application of the invention do not show any order, number or importance, but are only used to distinguish different constituent parts. Likewise, a term "a," "an," or the like does not indicate limitation in number, but specifies the presence of at least one. A term "comprises," "comprising," "includes," "including", "contains" or the like means that an element or article ahead of this term encompasses element(s) or article(s) listed behind this term and its(their) equivalents, but does not preclude the presence of other elements or articles. A term "connection," "coupled," or the like is not limited to physical or mechanical connection, but can include electrical connection, whether directly or indirectly. "Upper," "lower," "left," "right" or the like is only used to describe a relative positional relationship, and when the absolute position of a described object is changed, the relative positional relationship might also be changed accordingly.

Figure 1:
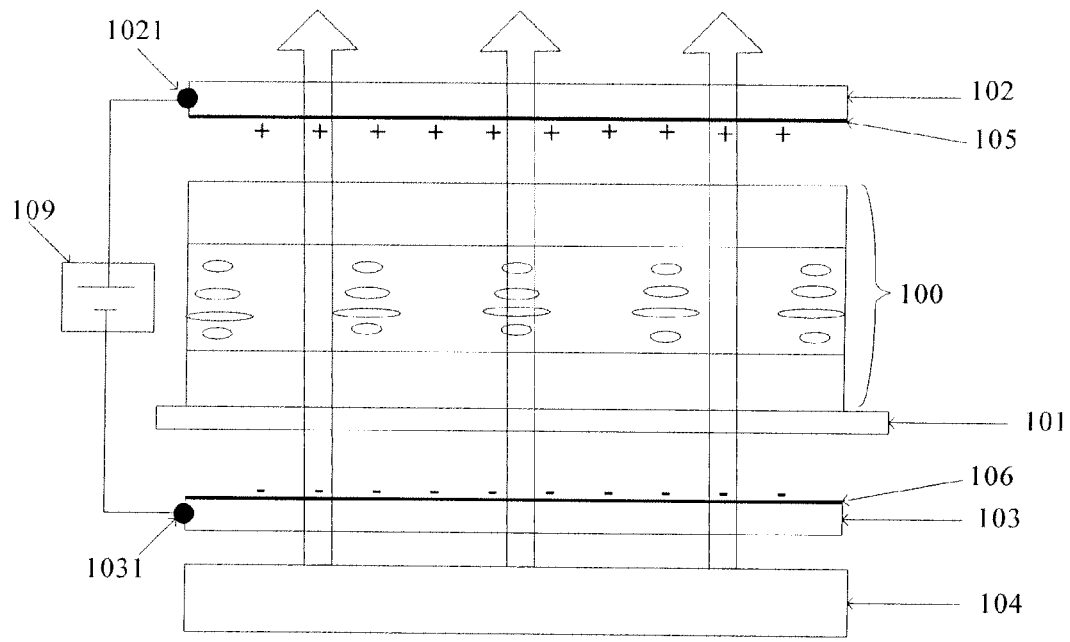
FIG. 1 is a structurally schematic view illustrating a detection device provided by an embodiment of the invention.

A device for detecting a liquid crystal display panel provided by an embodiment of the invention, as illustrated in FIG. 1, includes: a transparent bearing platform 101, for bearing a liquid crystal display panel 100 to be detected; a first polarizer 102, positioned over the transparent bearing platform 101; a second polarizer 103, positioned under the transparent bearing platform 101; a backlight source 104, located below the second polarizer 103. In operation, the light emitted upward from the backlight source 104 passes through the second polarizer 103 and the transparent bearing platform 101 and arrives at the first polarizer 102.

The device further includes: a first transparent electrode layer 105, provided over the transparent bearing platform 101; a second transparent electrode layer 106, provided under the transparent bearing platform 101; a signal loading unit 109, electrically connected to the first transparent electrode layer 105 and the second transparent electrode layer 106, for loading an electric signal to the first transparent electrode layer 105 and the second transparent electrode layer 106, so that an electric field for allowing liquid crystal molecules of a liquid crystal display panel 100 to be detected on the transparent bearing platform 101 to deflect is formed between the first transparent electrode layer 105 and the second transparent electrode layer 106.

In the embodiment, the first polarizer 102 and the second polarizer 103 are disposed at the upper and lower sides of the liquid crystal display panel 100 to be detected, respectively. Exemplarily, when an FFS mode liquid crystal display panel is detected, in the case where no electric field is applied to the liquid crystal display panel, the liquid crystal molecules are aligned parallel to the substrate, and the absorption axes of the first polarizer 102 and the second polarizer 103 are configured to cross with each other at 90 degrees. The absorption axis of the second polarizer 103 has the same orientation as the liquid crystal molecules, and the incident light proceeds forward linearly via the liquid crystal layer that is aligned in parallel, without changing the polarization direction, but cannot pass through the first polarizer, thus a black state of being transparent to light appearing at the light exiting side; in the case where an electric field is applied, the liquid crystal molecules will be twisted and a birefringence phenomenon happens to the liquid crystal layer, and thus, the polarization direction of the incident light is changed after passing through the liquid crystal layer, so that the incident light can pass through the first polarizer and, at the light exiting side, a state of being pervious to light appears.

In the embodiment as illustrated in FIG. 1, exemplarily, the first transparent electrode layer 105 may be a layer of transparent conductive film that is coated on the first polarizer 102, such as a nanometer ITO (Indium Tin Oxide) thin film, and moreover, a signal contact terminal 1021 is provided on the first polarizer 102. The second transparent electrode layer 106 may be a layer of transparent conductive film that is coated on the second polarizer 103, such as an ITO thin film, and moreover, a signal contact terminal 1031 is provided on the second polarizer 103. An ITO thin film has transparency and conductivity, and therefore, after the ITO thin film is coated on a polarizer, it will not affect operation of the polarizer.

Upon detection, an FFS mode liquid crystal display panel 100 to be detected that does not have an electrode terminal side is placed on the transparent bearing platform 101; the backlight source 104 is turned on; an electric signal is applied to the signal contact terminal 1021 on the first polarizer 102 and the signal contact terminal 1031 of the second polarizer 103, so that between the first transparent electrode layer 105 on the first polarizer 102 and the second transparent electrode layer 106 on the second polarizer 103, there is produced a planar electric field, which allows the liquid crystals of the liquid crystal display panel 100 situated therein to deflect. As such, the light emitted from the backlight source 104 can pass through the liquid crystal display panel 100, and then, defectives that might exist in the product can be found by visual inspection, and the quality management of products of the FFS type is strengthened.

Figure 2:
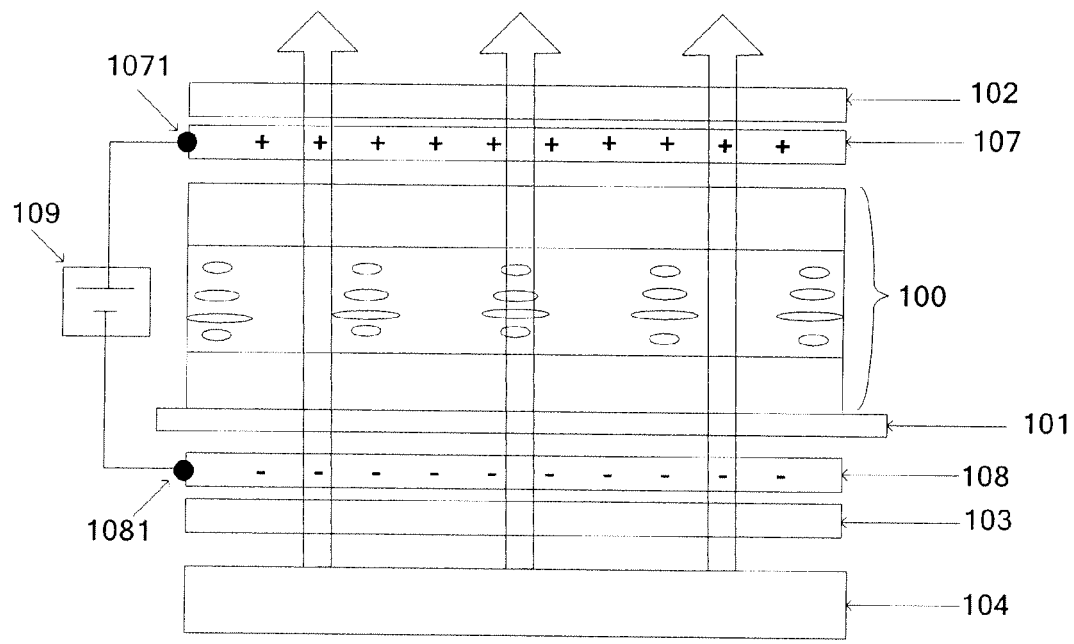
FIG. 2 is a structurally schematic view illustrating a detection device provided by another embodiment of the invention.

Preferably, in another embodiment of the invention, the first transparent electrode layer may be a first transparent glass substrate 107 on which a transparent conductive film (such as an ITO thin film) is coated, as illustrated in FIG. 2. The first transparent glass substrate 107 may be located between the transparent bearing platform 101 and the first polarizer 102, and the area of the first transparent glass substrate 107 may be larger than or equal to the area of the liquid crystal display panel 100 to be detected. A signal contact terminal 1071 is provided on the first transparent glass substrate 107. The second transparent electrode layer may be a second transparent glass substrate 108 on which a transparent conductive film (such as an ITO thin film) is coated. The second transparent glass substrate 108 may be located between the transparent bearing platform 101 and a second polarizer 103, and the area of the second transparent glass substrate 108 may be larger than or equal to the area of the liquid crystal display panel 100 to be detected. A signal contact terminal 1081 is provided on the second transparent glass substrate 108.

Similar to the previous embodiment, upon detection, an FFS mode liquid crystal display panel 100 to be detected that does not have an electrode terminal side is placed on the transparent bearing platform 101; a backlight source 104 is turned on; an electric signal is applied to the signal contact terminal 1071 on the first transparent glass substrate 107 and the signal contact terminal 1081 of the second transparent glass substrate 108, so that between the first transparent glass substrate 107 and the second transparent glass substrate 108, there is produced a planar electric field, which allows liquid crystals of the liquid crystal display panel 100 situated therein to deflect. As such, the light emitted from the backlight source 104 can pass through the liquid crystal display panel 100, and then, defectives that might exist in the product can be found by visual inspection, and the quality management of products of the FFS type is strengthened.

It should be noted that, a transparent glass substrate on which an ITO thin film is coated being used as an electrode layer will not affect manufacture of the polarizer, will not make the manufacturing process complicate, and will not affect optical effects of the polarizer, either. Furthermore, the production of the transparent glass substrate as the electrode layer is extremely simple. In the course of detection, the only thing to do is to incorporate the transparent glass substrate provided with the ITO thin film to which a signal is applied directly into an original detecting device, and this makes the cost of detection reduced. In the embodiment of the invention, the transparent glass substrate with the conductive thin film may also be another transparent substrate that is conductible per se, preferably, a thin transparent substrate.

According to another embodiment of the invention, there is provided a method for detecting a liquid crystal display panel; over a transparent bearing platform, there is provided a first polarizer; under the transparent bearing platform, there is provided a second polarizer; below the second polarizer, there is provided a backlight source; above the transparent bearing platform, there is provided a first transparent electrode layer; under the transparent bearing platform, there is provided a second transparent electrode layer; and, a signal loading unit is provided to connect to the transparent electrode layer and the second transparent electrode layer. The detection method comprises the following steps.

S301, the liquid crystal display panel to be detected is loaded onto the transparent bearing platform.

S302, an electric signal is loaded to the first transparent electrode layer and the second transparent electrode layer by the signal loading unit, so that an electric field allowing liquid crystal molecules to deflect is formed between the first transparent electrode layer and the second transparent electrode layer.

For example, it is possible that a voltage signal is loaded to the first transparent electrode layer and the second transparent electrode layer by the signal loading unit, so that a voltage difference, such as in the range between 3V and 8V or so, is established between the first transparent electrode layer and the second transparent electrode layer. Then, an electric field to make liquid crystal molecules deflect is formed between the first transparent electrode layer and the second transparent electrode layer, and in turn, the liquid crystals are deflected and arranged regularly under the action of the electric field, thereby allowing light to pass therethrough.

S303, the light from the backlight source is allowed to transmit through the second polarizer and the transparent bearing platform to arrive at the first polarizer.

The polarization directions of the polarized light filtered by the first polarizer and the polarized light filtered by the second polarizer are parallel, and when the liquid crystal molecules are deflected and arranged regularly under the action of the electric field, the light can pass through the second polarizer, and then pass through the transparent bearing platform to arrive at the first polarizer.

S304, detection is conducted on the liquid crystal display panel with the light arriving at the first polarizer.

When the light from the backlight source arrives at the first polarizer, owing to different deflection directions of liquid crystals, the polarization state of the light arriving at the first polarizer also differs. If a defective that may affect the aperture ratio of a pixel exists in the pixel of the liquid crystal display panel, then when the light emitted from the backlight source passes through the defective pixel, the amount of the transmitted light will be more or less than that in the normal condition. Thereby, difference in light intensity of display occurs. So, whether a defective exits or not can be determined in accordance with the change of brightness of the received light.

With respect to the method for detecting the liquid crystal display panel provided by the embodiment of the invention, a planar electric field is introduced into the device, and when an FFS mode liquid crystal display panel is detected, by applying electric signals across the liquid crystal display panel, the planar electric field is formed to make liquid crystal molecules in the liquid crystal display panel deflect, allowing the light emitted from a backlight source to pass through liquid crystals. Thus, detection on the liquid crystal display panel is realized, and yield is enhanced.

The descriptions made above are merely exemplary embodiments of the invention, but are not used to limit the protection scope of the invention. The protection scope of the invention is determined by attached claims.

The invention claimed is:

1. A device comprising:
a transparent bearing platform for bearing the liquid crystal display panel to be detected;
a first polarizer, positioned over the transparent bearing platform;
a second polarizer, positioned under the transparent bearing platform;
a backlight source, positioned below the second polarizer, wherein light emitted from the backlight source is capable of arriving at the first polarizer after passing through the second polarizer and the transparent bearing platform;
a first transparent electrode layer, provided over the transparent bearing platform;
a second transparent electrode layer, provided under the transparent bearing platform; and
a signal loading unit, electrically connected to the first transparent electrode layer and the second transparent electrode layer, for loading an electric signal to the first transparent electrode layer and the second transparent electrode layer, so that an electric field is generated between the first transparent electrode layer and the second transparent electrode layer, liquid crystal molecules of the liquid crystal display panel to be detected on the transparent bearing platform are deflected under control of the electric field;
wherein the first transparent electrode layer is a first transparent glass substrate on which a transparent conductive film is coated; an area of the first transparent glass substrate is larger than an area of the liquid crystal display panel to be detected; and
wherein the second transparent electrode layer is a second transparent glass substrate on which a transparent conductive film is coated; an area of the second transparent glass substrate is larger than an area of the liquid crystal display panel to be detected.

2. The device according to claim 1, wherein the first polarizer and the second polarizer are disposed at an upper side and a lower side of the liquid crystal display panel to be detected, respectively, and absorptions axes of the first polarizer and the second polarizer are configured to cross at 90degrees.

3. The device according to claim 1, wherein the first transparent electrode layer is a transparent conductive film coated on the first polarizer; and a signal contact terminal is provided on the first polarizer.

4. The device claimed according to claim 1, wherein the second transparent electrode layer is a transparent conductive film coated on the second polarizer; and a signal contact terminal is provided on the second polarizer.

5. The device according to claim 1, wherein a signal contact terminal is provided on the first transparent glass substrate.

6. The device according to claim 5, wherein the first transparent glass substrate is located between the transparent bearing platform and the first polarizer.

7. The device according to claim 1, wherein a signal contact terminal is provided on the second transparent glass substrate.

8. The device according to claim 7, wherein the second transparent glass substrate is located between the transparent bearing platform and the second polarizer.

9. The device according to claim 5, wherein a signal contact terminal is provided on the second transparent glass substrate.

10. The device according to claim 9, wherein the second transparent glass substrate is located between the transparent bearing platform and the second polarizer.

* * * * *